(12) United States Patent
Beuvry et al.

(10) Patent No.: US 6,653,288 B1
(45) Date of Patent: Nov. 25, 2003

(54) INJECTABLE ANTHELMINTIC COMPOSITIONS AND METHODS FOR USING SAME

(75) Inventors: Vincent Beuvry, Opio (FR); Georges Bufala, Antibes (FR); Guy Derrieu, Cagnes sur Mer (FR)

(73) Assignee: Virbac S.A., Carros (FR)

( * ) Notice: Subject to any disclaimer, the term of this patent is extended or adjusted under 35 U.S.C. 154(b) by 0 days.

(21) Appl. No.: 10/259,596

(22) Filed: Sep. 30, 2002

(51) Int. Cl.⁷ .................. A01N 43/04; A01N 25/00; A61K 31/70
(52) U.S. Cl. .................. 514/28; 514/943; 424/422
(58) Field of Search ................. 514/28, 943; 424/422

(56) References Cited

U.S. PATENT DOCUMENTS

| | | | |
|---|---|---|---|
| 3,239,345 A | | 3/1966 | Hodge et al. |
| 3,950,360 A | * | 4/1976 | Aoki et al. ................. 549/264 |
| 4,199,569 A | * | 4/1980 | Chabala et al. ............... 514/30 |
| 4,778,821 A | | 10/1988 | Clough et al. |
| 5,288,496 A | | 2/1994 | Lewis |
| 5,332,577 A | | 7/1994 | Gertner et al. |
| 5,419,910 A | | 5/1995 | Lewis |
| 5,686,092 A | | 11/1997 | Lewis |
| 5,733,566 A | | 3/1998 | Lewis |
| 6,174,540 B1 | | 1/2001 | Williams et al. |
| 2002/0064547 A1 | | 5/2002 | Chern et al. |

FOREIGN PATENT DOCUMENTS

| | | |
|---|---|---|
| BE | 675 969 | 6/1966 |
| EP | 0 413 538 | 2/1991 |
| EP | 0 535 734 | 4/1993 |
| EP | 1 177 785 | 2/2002 |

OTHER PUBLICATIONS

D. L. Bransby, Bovine, pp. 16–19, "Steer Weight Gain Responses to Ivermectin when Grazing Fescue", May/Jun. 1997.
D. Bransby, et al., Highlights of Agricultural Research, vol. 45, No. 2, pp. 1–3, "Bolus Bonus IVOMEC SR Bolus Dewormer Boosts Weight Gains in Cattle", 1998.
R. J. Heitzman, Journal of Annual Science, vol. 57, No. 1, pp. 233–238, "The Absorption, Distribution, and Excretion of Anabolic Agents", 1983.
M. J. Kennedy, et al., Can. Vet. J., vol. 30, pp. 346–347, "Effect of Ivermectin on Weight Gains of Yearling Steers on Pasture in Central Alberta", Apr. 1989.
M.J. Kennedy, et al., Can. Vet. J., Vol. 29, pp. 566–568, "Evaluation of Ivermectin on Performance of Beef Cattle on Pasture in Alberta", Jul. 1988.
J. van der Vies, WMW, pp. 366–368, "1.3 Pharmacokinetics of Anabolic Steroids", 1993.

* cited by examiner

*Primary Examiner*—James O. Wilson
*Assistant Examiner*—LaTonia M. Fisher
(74) *Attorney, Agent, or Firm*—Oblon, Spivak, McClelland, Maier & Neustadt, P.C.

(57) ABSTRACT

Injectable compositions containing a liquid solvent free of solid polymers, anthelmintic agent(s) and hormonal growth promoter(s), where the anthelmintic agent(s) and the hormonal growth promoter(s) are dissolved in the polymer free solvent system. The present invention additionally relates to methods of promoting animal growth and inhibiting parasitic infection/infestation with these compositions, as well as methods of preparing such compositions.

46 Claims, No Drawings

INJECTABLE ANTHELMINTIC COMPOSITIONS AND METHODS FOR USING SAME

BACKGROUND OF THE INVENTION

Field of the Invention

The present invention relates to injectable compositions containing a liquid solvent free of solid polymers, anthelmintic agent(s) and hormonal growth promoter(s), the anthelmintic agent(s) and the hormonal growth promoter(s) are dissolved in the solvent. The present invention additionally relates to methods of promoting animal growth and treating and/or preventing parasitic infection/infestation with these compositions, as well as methods of preparing such compositions.

DESCRIPTION OF THE BACKGROUND

To a great extent, the pituitary gland and its secretions of growth or somatotrophic hormone regulate animal growth. Anabolic implants increase (via the pituitary gland) growth hormone and insulin at the cellular level, resulting in increased synthesis of muscle tissue, and frequently, reduced deposition of body fat. The result is usually increased growth rate and improved feed efficiency.

Certain growth promoting hormones have been approved for use at very low concentrations to increase the rate of weight gain and/or improve feed efficiency in beef cattle. The livestock producer generally administers hormonal growth-promoting drugs at specific stages of production. Residual levels of these hormones in food have been demonstrated to be safe, as they are well below any level that would have a known effect in humans.

Estradiol, progesterone, and testosterone are naturally-occurring (endogenous) steroid hormones produced in significant quantities throughout the lifetime and are required for the proper physiological functioning and maturation of every mammal. All endogenous steroid hormone products marketed in the U.S. and in many other countries for beef growth-promotion are formulated as implantable pellets and are designed to deliver the hormones at a slow, constant rate when injected subcutaneously under the skin of the animal's ear. Numerous scientific studies have demonstrated that when these drugs are used in accordance with their approved conditions of use, concentrations of the hormones in edible tissues remain within the normal physiological range that has been established for untreated animals of the same age and sex. Consumers are not at risk from eating food from animals treated with these compounds because the amount of added hormone is negligible compared to the amount normally found in the edible tissues of untreated animals and that are naturally produced by the consumer's own body.

Unlike naturally occurring steroid hormones, there is no natural production of the synthetic compounds, trenbolone acetate, zeranol, and melengestrol acetate (MGA). Zeranol and its metabolites β-zearalanol and zearalanone, and zearalenone, and its metabolites β-zearalenol and α-zearalenol, are members of the class of compounds known as resorcyclic acid lactones.

To obtain a prolonged effect of the action of growth-promoting hormones, which is an essential condition to allow these substances to play the role of anabolic agents, several modes of administration were envisaged such as: Intramuscular injections of oily suspensions of these substances as esters: acetate, propionate, benzoate: Intramuscular injections of aqueous suspensions of micro-crystals of active products: Subcutaneous administration of implant in which the active is placed.

Some implants are "matrix" type, and consist of an active compound dispersed in a matrix of carrier material. The carrier material may be porous or non-porous, solid or semisolid, and permeable or impermeable to the active compound. Matrix devices may be biodegradable, i.e. they may slowly erode after administration. Alternatively, matrix devices may be non-degradable, and rely on diffusion of the active compound through the walls or pores of the matrix. Other devices are "reservoir" type, and consist of a central reservoir of active compound surrounded by a rate controlling membrane (rcm). The rcm may be either porous or non-porous, but is not usually biodegradable. However, reservoir devices often suffer from an inadequate rate of delivery: the rcm surface area required maintaining an effective concentration of active compound is frequently so large that it is impractical to administer the device. Additionally, reservoir devices are sensitive to rupture: if the rcm is breached, an excessive (possibly lethal) dose of active compound may be released instantaneously. Some sustained release devices are hybrids, having a matrix core surrounded by a rcm. Other sustained release devices may be mechanical in nature, and include small compound-filled electrical or osmotic pumps. While these devices may be capable of zero order release, they are typically too expensive to compete economically with matrix and reservoir devices.

Implantation is the most commonly used method to administer growth-promoting hormones, even if several are active after oral administration.

Implants are widely used in veterinary medicine and often consist of compressed pellets or silicone-containing rubber. The active substances are dispersed in the solid rubber or located inside a hollow rubber body. The release rate of the active substances from the implant, and hence the period for which the implant is effective, are generally determined by the accuracy of the calibration (amount of active ingredient in the implant) of the implant, the environment of the implant and the polymer formulation from which the implant is made. Growth promoting implants commercially available are applied to the ears of cattle. Implanting elsewhere may be ineffective and result in condemnation of the carcass.

Animals, particularly calves, should be implanted two or more times during the growth period. Maximum benefit is obtained by having an approved, viable growth implant in cattle for most (or all) of their life from birth to harvest.

During implantation of implants in animals, conditions are typically unsanitary, causing infection, which can result in loss of implants. Use of an antibiotic or germicide layer or coating on the surface of the implant to reduce infections and to improve implant retention has often been adopted. The antibiotic coating facilitates parenteral administration of the implants under non-sterile conditions; requirements for cleaning the implant needle, the site of implantation on the animal, and the implantation device are minimized. However, this leads to introduce an antibiotic active agent into the composition, what has the effect of increasing the risks of resistance to the antibiotic and of complicating the manufacture of the implant.

The implanting technique must be done properly to obtain the greatest response and avoid undesirable side effects. One has to be especially careful to follow recommendations on correct implant usage, implant replacement, and implanting technique. For example, the animal has to be properly restrained in a squeeze chute or headgate to allow access to the ear, the implant has to be deposited between the skin and cartilage on the back side of the ear and below the midline of the ear, the implant must not be placed closer to the head than the edge of the cartilage ring, farthest from the head, which essentially means it must be placed in the middle one-third of the ear. Proper procedures for using implants, which are non-sterile injectable devices, require to cleanse the skin at the implant insertion site, to avoid placing an implant at the site of an old implant or other injury or in an area that will be used for an ear tag, to avoid crushing implants, to avoid injuring major blood vessels of the ear, to disinfect the implant needle between applications. The tissue irritation caused by an undiluted disinfectant can cause the expulsion of an implant or the formation of scar tissue that could interfere with the effective release of growth promotant from the implant and care should be taken when selecting an implant needle cleaning solution. Some breeders coat the cleaned implanting needle with an approved, non-irritating antibiotic between animals as an additional safeguard to help prevent implant site infections. It is also important to visually inspect and physically palpate the implant site after the implant is administered to ensure the implant is properly placed and all the pellets in the pelleted implants are properly aligned.

In addition, implants contain determinate quantities of growth-promoting hormones and therefore do not permit to adjust precisely the dose to the weight of the animal treated.

Since they are slow release or controlled release devices, at time of slaughter, the ear may still contain 20% of the administered hormone. Because of this, the ear must be discarded at slaughter.

It is thus acknowledged that the administration of implants presents constraints and risks: access to the ear, precise site of administration, risk of deterioration of the cartilage, risk of scarification, risks of fall of the implant, risks of damage of tissues, risks of infection because of non sterile devices. These risks are multiplied by the re-implantation, which is necessarily done in the same zone.

Furthermore, side effects may occur: implanting too close to the head or crushing the pellet during implantation will contribute to side effects such as bulling and rectal and vaginal prolapses.

It is preferable for cattle to be free from parasites and to obtain adequate and balanced nutrition in order to receive the full benefit of the implant.

The effects of parasitism can be separated into two types: subclinical and clinical. Losses in animal productivity (weight gain, altered carcass composition, conception rate, etc.) are all subclinical effects; whereas, visible disease-like symptoms (roughness of coat, anemia, edema, diarrhea) are clinical effects. The subclinical effects are of major economic importance to the producer.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often serious infection in various species of animals.

The most common genera of nematodes infecting the animals referred to above are Haemonchus, Trichostrongylus, Ostertagia, Nematodirus, Cooperia, Ascaris, Bunostomum. Oesophagostomum, Chabertia, Trichuris, Strongylus, Trichonema, Dictyocaulus, Capillaria, Heterakis, Toxocara, Ascaridis, Oxyuris, Ancylostoma, Uncinaria, Toxascaris and Parascaris. Certain of these, such as Nematodirus, Cooperia and Oesophagostomum, attack primarily the intestinal tract. Others, such as Haemonchus and Ostertagia are more prevalent in the stomach. Others, such as Dictyocaulus, are found in the lungs. Still other parasites may be located in other tissues and organs of the body such as the heart and blood vessels, subcutaneous and lymphatic tissue, and the like.

In particular, cattle can be infected by roundworms (nematodes) which are generally considered the most economically devastating internal parasites of livestock. The medium or brown stomach worm (*Ostertagia ostertagi*) and the Cooperia species are the most common roundworms. Although cattle can be infected with tapeworms, their effect on animal performance is minimal compared to the roundworms. Problems associated with flukes also occur. Protozoans such us Coccida are another type of internal parasites.

The parasitic infections known as helminthiases lead to anemia, malnutrition, weakness, weight loss, severe damage to the walls of the intestinal tract and other tissues and organs, and, if left untreated, may result in death of the infected host.

Many antiparasitic products are on the market. Most of the products are either avermectins/milbemycins (invermectin, abamectin, doramectin, eprinomectin, moxidectin). Or benzamidazoles (oxfendazole, albendazole, fendbenzdazole). Avermectins/milbemycins provide an additional benefit of external parasite control plus internal parasite control, as well as persistent protection for days to weeks after treatment. External parasites such as ticks, fleas, louses and scabies are also responsible for losses in animal productivity.

Avermectins have been isolated as microbial metabolites from the microorganism *Streptomyces avermitilis* (U.S. Pat. No. 4,310,519) and can occur predominately as a mixture consisting of eight components (I. Putter et al. Experentia 37 (1981) p. 963, Birkhauser Verlag (Switzerland).

There is also interest in the synthetic derivatives, especially 22,23 dihydroavermectin $B_1$, (ivermectin) (U.S. Pat. No. 4,199,569). Similarly, milbemycin B-41 D has been isolated by fermentation from *Streptomyces hygroscopicus* (cf. "Milbemycin: Discovery and Development" I, Junya et al. Annu. Rep. Sankyo Res. Lab. 45 (1993), pp. 1–98; JP Pat 8 378 549; GB 1 390 336).

The use of avermectins, 22,23 dihydroavermectins $B_1$, (ivermectins) and milbemycins, from the class of the macrocyclic lactones as endoparasiticides has been known for a long time and is the subject of numerous patent applications and review articles (e.g. Biological effects in: "Ivermectin and Abamectin" W. C. Campbell, Ed., Springer Verlag, New York, N.Y., 1989; "Avermectins and Milbemycins Part II" II. G. Davies et al. Chem. Soc. Rev. 20 (1991) pp. 271–339; Chemical modifications in: G. Luckas et al. (Eds.), Springer-Verlag, N.Y., (1990), Chapter 3: Cydectin.™. [moxidectin and derivatives]: G. T. Carter et al. J. Chem. Soc. Chem. Com-mun. (1987), pp. 402–404): EP 423 445-A1). The use of Doramectin (Pfizer) as an endoparasiticide is also known (ef. "Doramectin, a potent novel endectocide" A. C. Goudie et al. Vet. Parasitol. 49 (1993), pp. 5–15).

A common route of administration for the treatment of parasitic infection is the oral route. Antiparasitic compounds thus are administered orally to a unit-dosage form such as a capsule, bolus, or tablet or as a liquid drench. The drench is normally a solution suspension or dispersion of the active ingredient, usually in water, together with a suspending agent. Active parasitic agents are also administered via animal foodstuffs where the compound is intimately dispersed in the feed or used as a top-dressing, or in the form of pellets which may then be added to the finished feed or, optionally, fed separately.

Antiparasitic compounds are also administered parenterally, for example, by intraluminal, intramuscular, intratracheal, or subcutaneous injection in which the active ingredient is dissolved or dispersed in a liquid carrier vehicle. Antiparasitic agents are also administered topically in the form of ointments, powders, and liquids absorbed through the skin (i.e., transdermally).

The economic benefit of the use of these antiparasitic agents is largely recognized. The effect of the avermectins or the milbemycins on the weight gain and animal productivity has been particularly studied in cattle. It comes out in particular from these studies that two consecutive treatments, in general with an interval of five to ten weeks, are necessary so that one can observe significant weight gain arising only after the second treatment [see Kennedy & ZoBell, Can. Vet. J., 29, 566–568 (1988); Kennedy, ZoBell & Goonewardene. Can. Vet. J., 30, 346–347 (1989)]. It has also been observed in some experiments that treatment of steers grazing fescue, infected with the fungus Acremonium coenophialum, with ivermectin provides significant increases in weight gain while providing poor weight gain if fescue is non-infected. This suggests that ivermectin could have some anti-fescue toxicosis effects beside its anthelmintic action.

The simultaneous use of an antiparasitic agent of the avermectins or the milbemycins family in a Pour-On or Bolus formulation and of an anabolic implant shows a weight gain similar or superior to that obtained after administration of one of both products only. [see Bransby, Large Animal Practice, vol. 18, n°3, 16–19 (1997); Bransby, Gamble, Dawkins, Burguess & Rawls, Highlights of Agricultural Research, vol. 45, n°2, Summer 1998].

The concomitant and dissociated administration of two pharmaceutical compositions in different formulations and galenic forms, the one containing the growth-promoting hormone and the other containing the antiparasitic agent is not practical. It requires for the breeder the manipulation and the administration of different products at different sites. It is therefore laborious, time consuming and it is not cost effective. Furthermore, depending on the galenic forms that are used for the antiparasitic agent and the breeding conditions, it may be inefficient in terms of improvement of weight gain and productivity of the animals.

It has been a goal to develop compositions containing the active agents in association in a single formulation so as to be able to administer them to the animal simultaneously.

European Pat. Appl. No. 1177785 (A2) to Kenison discloses a combination growth promoting pharmaceutical pellet implant which delivered doses of both a growth stimulating agent and a supplemental agent that enhance the growth produced by the growth stimulated agent. The supplemental agent may be a parasiticide. However, such an implant holds the aforementioned disadvantages of the implants.

U.S. Pat. No. 5,332,577 to Gertner discloses a pharmaceutical composition for use in the transdermal administration of a medicament to both humans and animals. Administration is by means of a matrix that comprise a porous, absorbent, perforate and flexible laminar solid support, having the composition absorbed thereon. The invention includes a device for use in transdermal administration, which comprises the matrix, possibly included in a multi-layer system providing a desired controlled or sustained release pattern for the medicament; as well as apparatus for applying a medicament non-adhesively to the skin of an animal, comprising a removal enclosure bearing such a matrix or device, the apparatus being arranged for non-invasive mounting onto an animal ear. The medicament comprises at least one member selected from a list comprising reproduction modulating agents and anthelmintics.

Biodegradable polymers have been used in parenteral controlled release formulations of bioactive compounds. In one approach the polymer is fabricated into microspheres that may be injected via syringe, and the bioactive compound is entrapped within the microspheres.

U.S. Pat. Nos. 5,419,910 and 5,288,496 to Lewis disclose and claim a microparticulate sustained-release delivery system for promoting growth in animals. The microparticles are comprised of a biodegradable polymeric matrix such as poly-d,l-lactic acid, polyglycolic acid and the like. The microparticles may separately encapsulate a steroid growth promotant and an antibiotic or an antiparasitic agent.

U.S. Pat. No. 5,733,566 to Lewis discloses and claim a microparticulate sustained-release delivery system for providing antiparasitic agents to animals and a method of treating parasitic infections in animals using such delivery systems. The microparticles are comprised of a biodegradable polymeric matrix such as poly-d,l-lactic acid, polyglycolic acid and the like. The microparticles may separately encapsulate a steroid growth promotant and an antibiotic. Compositions and methods are provided wherein more than one antiparasitic agent is delivered or an antiparasitic agent is administered with other bioactive agents such as growth promoters and antibiotics.

U.S. Pat. No. 5,686,092 to Lewis discloses and claim a microparticulate sustained-release delivery system comprising microparticles having a biodegradable polymeric matrix wherein a steroid growth promoter is microencapsulated. The composition further comprises an unencapsulated or separately microencapsulated anthelmintic. The anthelmintic may also be within the polymeric matrix. The patent discloses a method of promoting growth in animals comprising administration of the compositions.

This approach has not proved to be practical in part due to the difficulty in the manufacturing procedure for producing sterile and reproducible products, and the high cost of manufacturing.

In another approach the biodegradable polymer and the bioactive material are dissolved in a biocompatible water-miscible solvent to provide a liquid composition.

U.S. patent application Ser. No. 20,020,064,547 to Chern discloses and claims a liquid polymeric composition including a polymer such as poly(lactide-co-glycolide) copolymer in a mixture of hydrophilic and lipophilic solvents for the controlled release of hydrophobic bioactive substances for an extended time period and without "bursts" of drug release. When the liquid composition is injected into the body, the solvent dissipates into the surrounding aqueous environment, and the polymer is necessary to form a solid depot from which the bioactive material is released. It forms what the inventors define as "a semi-solid depot with a skin made of polymer". This disclosure provides an in situ formed film coated or encapsulated liquid implant capable of functioning as a delivery system of drugs, medicaments, and other biologically active agents.

None of the compositions and treatment modalities used or described above meets the need for an injectable simultaneous delivery system for hormone growth promoters and anthelmintic agents that overcome the problems encountered when using the existing sustained released compositions.

SUMMARY OF THE INVENTION

In view of the above-described state of the art, the objects of the invention are to provide a composition for the concomitant release of hormonal growth promoters and anthelmintic agents in animals in a manner which would more efficiently promote the growth of such animals and that combines the advantages of convenient administration, efficient drug utilization, avoid the maintenance of solid residues in the body of the animal, minimal handling, safe delivery for the growth promoting compounds and the anthelmintic agents, stability, easy and cost effective manufacturing procedure and minimal drug residue. Accordingly, an injectable solution, parenterally administrable, has been developed for the simultaneous release of at least one anthelmintic agent and at least one hormonal growth promoter in animals, which includes the advantages of an unexpectedly prolonged release of the active agents and low tissue residue of the actives agent in various organs and at the injection site at the end of the treatment.

The invention consists of a novel veterinary injectable composition for the delivery of an anthelmintic agent pertaining to the group consisting of avermectins, milbemycins or derivatives thereof in combination with a hormonal growth promoter. The invention provides the anthelmintic agents pertaining to the group consisting of avermectins, milbemycins or derivatives thereof and the hormonal growth promoters within a solvent system in which both actives agents are dissolved, where the solvent system is free of solid and film-forming polymers.

In one embodiment, the growth-promoting hormonal agent is selected from the group consisting of estradiol, estradiol benzoate, 17beta-estradiol, trenbolone acetate, zeranol, MGA, progesterone, testosterone and their derivatives or combinations thereof.

The invention further provides a method for delivering an anthelmintic agent pertaining to the group consisting of avermectins, milbemycins or derivatives thereof and a hormonal growth promoter. Compositions and methods are provided wherein a hormonal growth promoter and more than one anthelmintic agent pertaining to the group consisting of avermectins, milbemycins or derivatives thereof is delivered. Compositions and methods are also provided wherein an anthelmintic agent pertaining to the group consisting of avermectins, milbemycins or derivatives thereof and more than one hormonal growth promoter is delivered. Compositions and methods are also provided wherein at least one anthelmintic agent pertaining to the group consisting of avermectins, milbemycins or derivatives thereof and at least one hormonal growth promoter are administered with at least one proactive agents such as antibiotics, antiparasitic agents, vaccines, or any desired active agent. The additional bioactive agent(s) can be in solution or in suspension in the polymer free solvent. The invention thus provides a wide range of possible in vivo release of bioactive agents.

Another aspect of this invention relates to a process for making the above described compositions which comprises dissolving the anthelmintic agent pertaining to the group consisting of avermectins, milbemycins or derivatives thereof in a suitable solvent and dissolving the hormonal growth promoter in a suitable solvent, the solvent suitable for the dissolution of the anthelmintic agent and the solvent suitable for the dissolution of the hormonal growth promoter being the same or different.

The invention also provides a method of promoting growth, i.e., increasing the rate of weight gain and/or improving feed efficiency in animals wherein the method comprises administration, in amounts sufficient to promote growth in the animals, of an injectable composition comprising at least one anthelmintic agent pertaining to the group consisting of avermectins, milbemycins or derivatives thereof and at least one hormonal growth promoter, the anthelmintic agent and hormonal growth promoter being dissolved in a suitable solvent system.

Yet another aspect of this invention is directed to a method of simultaneously promoting growth and combating parasitic infections or infestations, both internal and external including parasitic conditions in animals for prophylactic or therapeutic purpose, the method comprising administering by injection an anthelmintic effective amount and a growth promoting effective amount of a composition comprising at least one anthelmintic agent pertaining to the group consisting of avermectins, milbemycins or derivatives thereof and at least one hormonal growth promoter, the anthelmintic agent and hormonal growth promoter being dissolved in a suitable solvent system.

The invention is useful in all animals including, but not limited to cattle, swine, horses, deer, sheep, goats, reindeer, camels, bison, and poultry.

The invention is particularly useful for promotion of growth in food animals.

Thus, in view of the description above, the present invention includes an injectable composition, comprising:
  a liquid solvent,
  at least one anthelmintic agent selected from the group consisting of avermectins, milbemycins, and derivatives thereof, and
  at least one hormonal growth promoter,
  wherein the anthelmintic agent and the hormonal growth promoter are dissolved in the solvent, and
  wherein the liquid solvent is free of solid or film-forming polymers.

The present invention also includes a method of promoting animal growth, comprising administering an effective amount of the composition described above to an animal.

In addition, the present invention includes a method of simultaneously promoting growth of an animal and inhibiting parasitic infections and/or infestations in an animal, comprising administering an effective amount of the composition described above to an animal.

Further, the present invention provides a method of preparing the composition described, comprising combining the liquid solvent, anthelmintic agent, and hormonal growth promoter.

A more complete appreciation of the invention and many of the attendant advantages thereof will be readily obtained as the same becomes better understood by reference to the following detailed description.

DETAILED DESCRIPTION OF THE INVENTION

In order to provide a clearer and consistent understanding of the specification and claims, including the scope to be given such terms, the following definitions are provided:

The term "hormonal growth promoter" refers to an agent selected from the group consisting of natural or synthetic steroid growth promoters or derivatives of resorcyclic acid lactones which promote anabolism or increase tissue growth.

By "promoting growth" or "increasing growth" is meant increasing the weight or weight again of an animal by an amount not found in an animal whose growth was not being "promoted".

The term "solvent" or "solvent system" refers to a liquid material. The solvent or solvent system may be composed of only one type of solvent or a mixture of two or more solvents may be used. Such a mixture may contain the individual solvent components in any desired ratio.

The term "administer" is intended to mean any method for introducing the compositions of the present invention into a subject by parenteral (intramuscular, intraperitoneal, or subcutaneous) introduction. When administration is for the purpose of treatment, administration may be either for prophylactic or therapeutic purpose. When provided prophylactically the substance is provided in advance of any symptom. The prophylactic administration of the substance serves to prevent or attenuate any subsequent symptom. When provided therapeutically the substance is provided at (or shortly after) the onset of a symptom. The therapeutic administration of the substance serves to attenuate any actual symptom.

The term "animal" is intended to mean any living creature that is a) susceptible to parasitic infection or infestation and thus susceptible to treatment by the administration of the agents of this invention and b) susceptible to experience the benefit of improving its weight gain for therapeutic purposes as well as productivity purposes. Foremost among such animals are food animals. However, the invention is not intended to be so limiting, it being within the scope of the present invention to apply the compositions of the invention to any and all animals which may experience the benefit of the compositions or methods of the invention. These include work animals, zoo animals or pets.

The term "food animal" is intended to mean any animal that is consumed as a source of protein in the diet of humans or other animals. Typical food animals include bovine animals, for example cattle; ovine animals, for example sheep; porcine, for example pig; fowl, for example chickens and turkeys; rabbit, and the like.

The term "antiparasitic agent" is intended to mean any agent that treats parasitic infection or infestation. Parasites include endoparasites and ectoparasites. Species include, but are not limited to, helminths, protozoans, annelids, and arthropods. Subspecies include nematode and acarids. Thus, antiparasitic agents include those effective against these parasites. Preferred agents include the anthelmintics, and especially nematocides.

The term "anthelmintic agent" is intended to mean any agent that treats parasitic infection or infestation by helminths.

An important feature of the present invention is that the solvent of the composition is free from solid or film-forming polymer materials. In particular, the solvent is free of the solid or film-forming polymers described in the Background of the Invention section above.

Another feature of the invention is that the hormonal growth promoter and the anthelmintics are in solution in the composition of the present invention, i.e., those active agents are dissolved in the solvent. However, additional active agents, such as described below, may be present in the composition in suspended form.

The present invention concerns a method of increasing growth in food animals which comprises providing to such animals, in amounts sufficient to promote growth in the animals, of an injectable composition comprising at least one anthelmintic agent pertaining to the group consisting of avermectins, milbemycins or derivatives thereof and at least one hormonal growth promoter, the anthelmintic agent and hormonal growth promoter being dissolved in a suitable solvent system. The method of the present invention provides advantages over methods known in the art such as, inter alia, an increased weight gain and a concomitant prevention and/or treatment of parasitic infections or infestations. The injectable system provides advantages such as convenient administration in terms of animal handling, safe delivery for the active ingredients since the composition is sterile, easy adjustment of the dose of the active ingredients to be delivered according to the weight of the animal, to avoid the risk of persistence of solid residues in the body of the animal, to prevent the loss of dose during treatment which often occurs with solid pellet implants, the ability to mix easily different drugs in a single formulation, minimal drug residue and efficiency of the growth promotion and deworming.

By choosing a suitable combination of at least one anthelmintic agent pertaining to the group consisting of avermectins, milbemycins or derivatives thereof and at least one hormonal growth promoter, both dissolved in a suitable solvent, it has been possible to enhance the penetration capacity of the hormonal growth promoter through the living tissue of the animal and maintain its bio availability in such a manner that, although the solvent was expected to drive to a "burst" of drug release and no maintained activity, the pharmacological effects of the hormonal growth promoter is maintained and may even be increased for an unexpected period of time.

Furthermore, it has surprisingly been found that the growth promotion activity of the composition according to the invention, if compared with the combined growth promotion activities of the individual compounds together forming the active ingredient of the composition of the present invention, may not only be additive, as can he expected in principle, but also can show a surprising, synergistic effect. In this connection, the term "synergistic effect" is neither limited to the pure growth promotion activity, nor is it necessary that this term relates at all to the pure growth promotion activity, but this term can relate to any property of the composition of the present invention, which is advantageous, if compared with the combined corresponding properties of the individual compounds, being in separate formulations, together forming the active ingredient of the composition of the present invention. As examples of such advantageous properties of the composition of the present invention there may be mentioned: a broadening in the spectrum of the parasiticidal activity towards additional or different parasites, for example towards a resistant parasite species; a reduction in the rates of application of one or both compounds; a sufficient degree of parasite control or weight gain by means of the composition of the present invention even in cases where the individual compounds together forming the active ingredient of the composition of the present invention are totally ineffective due to their extremely low rates of application; an advantageous behavior in the case of being formulated and/or applied, as for example bioavailability of one or both compounds; an improved storage stability; a better light stability; a better heat stability; an advantageous behavior in the case of being degraded; a better toxicology profile; an improved ecotoxicology behavior, other advantages familiar to those skilled in the art.

The invention consists in an injectable composition for the delivery of an anthelmintic agent pertaining to the group consisting of avermectins, milbemycins or derivatives thereof and a hormonal growth promoter, the anthelmintic agent and the hormonal growth promoter being dissolved in solvent system free of film-forming or solid polymers.

It is an essential feature of the present invention that the anthelmintic agent compound pertains to the group consisting of macrocyclic lactones i.e. avermectins, milbemycins or derivatives thereof. The avermectin and milbemycin series of compounds are potent anthelmintic and antiparasitic agents against a wide range of internal and external parasites. The compounds that belong to this series arc either natural products or are semi-synthetic derivatives thereof. The structure of these two series of compounds are closely related and they both share a complex 16-membered macrocyclic lactone ring; however, the milbemycin do not contain the aglycone substituent in the 13-position of the lactone ring. Naturally occurring milbemycins are described in Aoki et al., U.S. Pat. No. 3,950,360, incorporated herein by reference, as well in the various references cited in "The Merck Index" 12. sup.th ed., S. Budavari, Ed., Merck & Co., Inc. Whitehouse Station, N.J. (1996), incorporated herein by reference. Semisynthetic derivatives of these classes of compounds are well known. Such compounds encompass, but are not limited to ivermectin, abamectin, doramectin, eprinomectin, sclamectin, milbemycin oxime, and moxidectin. Doramectin and ivermectin will be particularly preferred.

Suitable growth promoters include estradiol, 17beta-estradiol, estradiol benzoate, trenbolone acetate, zeranol, MGA, testosterone, their derivatives and any combination thereof.

Preferably the hormonal growth promoter is zeranol, a combination of estradiol benzoate and trenbolone acetate or a combination of estradiol benzoate and testosterone propionate.

The solvent system of the present invention will be any suitable solvent wherein at least one anthelmintic agent pertaining to the group consisting of avermectins, milbemycins or derivatives thereof and at least one hormonal growth promoter are dissolved in an appropriate solvent system free of solid or film-forming polymers in the resulting composition.

The solvents forming the solvent system of the present composition can be any biologically or physiologically or medically or veterinarily acceptable and polymeric free (meaning essentially free of any solid or film-forming polymeric material) solvent.

In one embodiment, the solvent forming the solvent system is a hydrophilic solvent, e.g., water-miscible preferably those when mixed with water in a ratio from 1:9 to 9:1 form a single-phase solution. Examples of the hydrophilic solvent suitable for the present invention include, but are not limited to PEG, polyglycols such as propylene glycol, polyethylene glycol 200, polyethylene glycol 300 and polyethylene glycol 400, di(ethylene glycol)ethyl ether, isopropylidene glycerol, dimethyl isosorbide, propylene carbonate, glycerol, glycofural, di(propyleneglycol) methyl ether, pyrrolidones such as N-methyl pyrrolidone and 2-pyrrolidone, and mixtures thereof. Other solvents may also be useful as the hydrophilic solvent such as for instance C2 to C6 alkanol (e.g., ethanol, propanol, butanol), acetone, alkyl esters such as methyl acetate, ethyl acetate, ethyl lactate, alkyl ketones such as methyl ethyl ketone, dialkylamides such as dimethylformamide, dimethyl sulfone, tetrahydrofuran, cyclic alkyl amides such as caprolactam, oleic acid, aromatic amides such as N,N-diethyl-m-toluamide, and 1-dodecylazacycloheptan-2-one. The hydrophilic solvent can be a mixture of solvents. Other suitable solvents can include: glycol ethers such as propylene glycol monomethyl ether, dipropylene glycol monomethyl ether and diethylene glycol ethyl ether, di(ethylene glycol)ethyl ether acetate, di(propylene glycol)methyl ether, di(propylene glycol)methyl ether acetate, glycerol formal, glycofurol. Mono- and di-alkyl esters such as isopropyl myristate, mono-, di- and tri-alkylamides such as N,N,-dimethylacetamide, and polar, aprotic solvents such as mono- and dialkyl sulfoxides such as DMSO and decylmethylsulfoxide. Mixtures of these in any proportion may be used.

The present invention is also directed to a method of stimulating growth in food animals by administering an injectable composition comprising an anthelmintic agent pertaining to the group consisting of avermectins, milbemycins or derivatives thereof and a hormonal growth promoter, the anthelmintic agent and the hormonal growth promoter being dissolved in a suitable solvent system The invention is further directed to a method of simultaneously promoting growth and combating parasitic infections or infestations, both internal and external including parasitic conditions in animals for prophylactic or therapeutic purpose, by administering, in an anthelmintic effective amount and in a growth promoting effective amount, an injectable composition comprising an anthelmintic agent pertaining to the group consisting of avermectins, milbemycins or derivatives thereof and a hormonal growth promoter, the anthelmintic agent and the hormonal growth promoter being dissolved in a suitable solvent system.

Therefore, the solvents forming the solvent system of the present methods can be any biologically or physiologically or medically or veterinarily acceptable water miscible solvents. In one embodiment of the present invention, the solvent system is essentially consisting in a hydrophilic solvent as described above.

The solvent system may alternatively be a mixture of hydrophilic solvents as described above and hydrophobic solvents, e.g., water-immiscible solvents, preferably with a solubility in water of less than 10% at room temperature. The resulting solvent system should have a hydrophilic character, e.g., be water dispersible (no partition between water and the solvent system when mixed). Preferably, the ratio between the hydrophilic solvent and the hydrophobic solvent may vary from 60:40 to 99:1, more preferably 80:20 to 95:5.

The non-water-miscible or hydrophobic solvent may be chosen from triethyl entrate, Miglyol 812, Miglyol 840, Crodamol GTCC, triacetin or benzyl benzoate; and additional lipophilic solvents may be used, e.g., hydrophobic rate modifying agents or plasticizers such as fatty acids, triglycerides, triesters of glycerol, oils such as castor oil, soybean oil or other vegetable oils or derivatives thereof such as epoxidized or hydrogenated vegetable oils such as epoxidized soybean oil or hydrogenated castor oil, sterols, higher alkanols (e.g., C6 or higher), glycerin and the like. The hydrophobic solvent can be a mixture of solvents.

In one embodiment of the present method of stimulating growth in food animals, the solvent system consists essentially of a hydrophilic solvent.

The compositions according to the invention may be prepared by dissolving all the solid ingredients in the vehicle under normal manufacturing conditions used for sterile injectable products. The present composition may contain additional inert substances commonly used in parenteral formulations including, but not limited to stabilizing agents, preservative agents, antimicrobial agents, antioxidants, and the like.

In one embodiment, to prepare the formulations of the present invention the active ingredients are dissolved in glycerol formal and, when dissolution is complete, the remaining solvents are added to prepare the final concentration of drug and ratio of solvents. Since the composition is for parenteral uses it must be sterilized, thus the final step is sterilization, preferably by non-heating means since the active ingredients might be subject to decomposition at autoclave temperatures. Membrane filtration is the preferred means of sterilization.

The formulations of the present invention contain a hormonal growth promoter and an anthelmintic agent pertaining to the group consisting of avermectins, milbemycins or derivatives thereof in are dissolved in an appropriate solvent system. The amount of hormonal growth promoter agent incorporated in the composition usually ranges from less than 0.2 wt % to as high as 20 wt %, preferably 0.5 to 5 wt %. The amount of anthelmintic agent incorporated in the composition usually ranges from less than 0.2 wt % to as high as 20 wt %, preferably 0.5 to 5 wt %. By weight % is meant parts of drug per parts of solvent by weight. For example, 10 wt % would mean 10 parts drug per 90 parts solvent by weight. Preferably, the ratio between the hormonal growth promoter agent and the anthelmintic agent may vary from 5:95 to 95:5, preferably from 20:80 to 80:20, more preferably less than or equal to 1:1.

Compositions and methods are provided wherein a hormonal growth promoter and more than one anthelmintic agent pertaining to the group consisting of avermectins, milbemycins or derivatives thereof is delivered. Compositions and methods are also provided wherein an anthelmintic agent pertaining to the group consisting of avermectins. milbemycins or derivatives thereof and more than one hormonal growth promoter is delivered. Compositions and methods are also provided wherein at least one anthelmintic agent pertaining to the group consisting of avermectins, milbemycins or derivatives thereof and at least one hormonal growth promoter are administered with other bioactive agents such as antibiotics, antiparasitic agents, vaccines, or any desired active agent. The additional bioactive agent(s) can be in solution or in suspension in the solvent system. The invention thus provides a wide range of possible in vivo release of bioactive agents.

Examples of antibiotics include, but are not limited to, oxytetracycline, tetracycline, ampicillin, gentamicin, penicillin, tylosin, erythromycin and spectinomycin.

Examples of antiparasitic agents include, but are not limited to, phenylpyrazole, nodulisporic acid, clorsulon and closantel.

Examples of vaccines include those which are of cellular, viral or bacterial origin, specifically *Pasteurella multocide, Pasteurella haemolytica, Haemophilus influenzae, Haemophilus ducreyi, Escherichia coli, Salmonella abortus ovis*, and IBR-BVD-P13 virus antigens.

Other active agents that are encompassed within the invention include, but are not limited to, vitamins such as Vitamin $B_{12}$, anti-inflammatory agents such as hydrocortisone, anaesthetic agents such as lidocaine chlorhydrate or tetracaine chlorhydrate, nonsteroid growth promoters such as bovine growth hormone and porcine growth hormone.

It would be well within the skill level of the practitioner to decide which additional bioactive agent(s) can be used in the inventive formulations. From the foregoing, the bioactive agent can be varied. The amount suitable for use in a formulation according to the invention can be determined by the skilled artisan without any undue experimentation from the knowledge in the art, and this disclosure, taking, into consideration factors typically considered by those skilled in the medical, veterinary or pharmaceutical arts, such as the species involved, the age, weight, general health, and sex of the animal, and the condition being treated and the LD50 and other characteristics of the bioactive substance(s).

In another aspect of the present invention there is provided a method for enhancing the penetration capacity of the hormonal growth promoter through the living tissue of an animal and maintain its bio availability, which comprises injecting animal with a liquid composition described herein. For this purpose, the composition comprises at least one anthelmintic agent selected from the group consisting of avermectins, milbemycins or derivatives thereof and at least one hormonal growth promoter, the anthelmintic agent and the growth promoter being dissolved in a solvent system.

The invention also provides a method of promoting growth in animals wherein the method comprises administration, in amounts sufficient to promote growth in the animals, of an injectable composition comprising at least one anthelmintic agent pertaining to the group consisting of avermectins, milbemycins or derivatives thereof and at least one hormonal growth promoter, the anthelmintic agent and the hormonal growth hormone being dissolved in the injectable composition. For this purpose, the anthelmintic agent is selected from the group consisting of avermectins, milbemycins or derivatives thereof, the amount of the anthelmintic agent being such that it ensure an increase of the weight or weight gain of the animal receiving the composition by a higher amount than the one expected when the animal is treated by the same composition not including the anthelmintic agent. The amount of the anthelmintic agent incorporated in the composition usually ranges from less than 0.2 wt % to as high as 20 wt % preferably 0.5 to 5 wt %.

The invention further provides a method of simultaneously promoting growth and combating parasitic infections or infestations, both internal and external including parasitic conditions in animals for prophylactic or therapeutic purpose, the method comprising administering by injection an anthelmintic effective amount and a growth promoting effective amount of a composition comprising at least one anthelmintic agent pertaining to the group consisting of avermectins, milbemycins or derivatives thereof and at least one hormonal growth promoter, the anthelmintic agent and hormonal growth promoter being dissolved in the injectable composition. For this purpose, the anthelmintic agent is selected from the group consisting of avermectins, milbemycins or derivatives thereof, the amount of the anthelmintic agent being such that it ensure it reduction of the target helminth burden in the animal of at least 90%, preferably more than 95% and more preferably 100%. The amount of the anthelmintic agent incorporated in the composition usually ranges from less than 0.2 wt % to as high as 20 wt %, preferably 0.5 to 5 wt %.

The compositions of the present invention are administered to a warm-blooded animal such as cattle, sheep, pigs, dogs, horses, cats, and the like (e.g., companion and feedstock animals) by intramuscular or subcutaneous injection. The formulations will generally be prepared to contain from 0.4 to 20%, preferably from 1 to 10% of the bioactive compound. For instance, at a preferred dose volume of about 1 ml to treat a cattle of 50 kg body weight the formulation contains from 50 to 100 mg of avermectin compound per ml of solution or about 5 to 10% w/v. However, depending upon the activity of the compound and the animal being treated, concentrations as low as 1% of bioactive compound are usable.

EXAMPLES

Having generally described this invention, a further understanding can be obtained by reference to certain specific examples which are provided herein for purposes of illustration only and are not intended to be limiting unless otherwise specified.

Example 1

Preparation of Injectable Composition Containing Abamectin and Trenbolone Acetate

| Ingredients | % w/v |
|---|---|
| Abamectin | 1.22 |
| Trenbolone acetate | 15.00 |
| Glycerol Formal | 60.00 |
| Propyl Gallate | 0.02 |
| Dithiopropionic Acid | 0.02 |
| EDTA | 0.01 |
| Monopropylene Glycol | To volume 100.00ml |

Example 1 is manufactured as follows:

1. To a clean dry mixing vessel add the glycerol formal 95% of the quantity of monopropylene glycol, propyl gallate, dithiopropionic acid, and EDTA while stirring add the abamectin and trenbolone acetate. Continue to stir until dissolved.

2. Make up to volume with the remaining 5% monopropylene glycol and stir well.

3. Sterilize product by suitable filtration, pack under sterile conditions into suitable injection vials and seal.

Example 1 produces a solution that is suitable for injection.

Example 2

Preparation of Injectable Composition Containing Progesterone and Oestradiol benzoate and Moxidectin

| Ingredients | % w/v |
|---|---|
| Moxidectin | 1.0 |
| Oestradiol benzoate | 0.5 |
| Progesterone | 5.0 |
| N-Methyl-Pyrrolidone | 60.0 |
| Butyl hydroxyanisole | 0.05 |
| Butyl hydroxytoluene | 0.05 |
| Sesame Oil | To volume 100.0 ml |

Example 2 is manufactured as follows:

1. To a clean dry mixing vessel add the N-Methyl-pyrrolidone, BHA, and BHT and while stirring add the moxidectin, oestradiol benzoate and progesterone.

2. Make up to volume with sesame oil and stir well.

3. Sterilize product by suitable filtration, pack under sterile conditions into suitable injection vials and seal.

Example 2 produces an oil-based solution that is suitable for administration as an injection.

Example 3

Preparation of Injectable Composition Containing Ivermectin and Zeranol

| Ingredients | % w/v |
|---|---|
| Ivermectin | 1 |
| Zeranol | 1 |
| Benzyl alcohol | 4 |
| Glycerol Formal | To volume 100 ml |

Example 3 is manufactured as follows:

1. To a clean dry mixing vessel add the glycerol formal and benzyl alcohol and while stirring add the ivermectin and zeranol. Continue to stir until dissolved.

2. Make up to volume with glycerol formal and stir well.

3. Sterilize product by suitable filtration, pack under sterile conditions into suitable injection vials and seal.

Example 3 produces a solution that is suitable for subcutaneous injection to cattle. It may be administered at a rate of 200 mcg/kg of ivermectin and 200 mcg/kg of zeranol (i.e. 1 ml./50 kg) of body weight of the animal.

The compositions of the invention are stable and have been shown to be non-toxic to animals.

Example 4

Stability Testing

The storage: stability of the composition prepared in Example 3 is evaluated by storing samples of the composition at 30° C. in an environmental chamber. The samples are removed periodically and visually inspected for physical changes in the appearance of the compositions. The results are summarized in Table 1.

TABLE 1

Physical Stability of Compositions

| Month | Appearance |
|---|---|
| 0 | clear solution |
| 1 | clear solution |
| 2 | clear solution |
| 3 | clear solution |
| 6 | clear solution |
| 12 | clear solution |
| 18 | clear solution |

As can be seen from the data in Table 1, the composition of the present invention is storage stable for at least 18 months.

Example 5

Zeranol Plasma Level Profiles of a Composition Comprising Ivermectin and Zeranol in Cattle Plasma levels of zeranol were determined in healthy cattle treated with the composition of Example 3 and compared to plasma levels of zeranol in healthy cattle treated simultaneously with commercial formulations (Ivomec® Injectable for Cattle containing 1% ivermectin and Ralgro® implants for Cattle containing 36 mg of zeranol). Sixteen animals (Holstein, generally weighing 196 to 250 kg) were divided into two groups. The composition according to Example 3 was given to one group as a single subcutaneous injection dosed at 0.2 mg/kg. The other group was implanted with one Ralgrog implant and subcutaneously injected with Ivomec® dosed at 0.2 mg/kg. Ten ml haparinized blood samples were collected from each treated animal on Days 3, 6, 10, 13, 16, 18, 21, 28, 35, 42, 56, 70, and 84. No statistical differences between the two groups have been observed in terms of Cmax (Maximal Plasmatic Concentration), MRT (Mean Residence Time) and AUC (Area Under Curve). It should be noted that in this trial $AUC_{0-42}$ corresponds to $AUC_{t,last}$ for most of the animals in both groups.

It can therefore be concluded that contrarily to what could be expected with a single injection or a composition according to the invention, no flash release of zeranol is observed in plasma of treated animals. Since the AUC of both treatments are not statistically different, the exposure of animals to zeranol in both groups is similar. Since the Cmax of both treatment are not statistically different, it may also be observed that the composition according to the invention provide a plasmatic concentration of zeranol that is well below any level that would drive to toxicity or side-effects in the animals.

Example 6

Tolerance Study of a Composition Comprising Ivermectin and Zeranol inCattle 152 animals were treated with the composition of Example 3 as a single subcutaneous injection dosed at 0.2 mg/kg. Local and general tolerance has been studied repeatedly for a week. No side effects were observed.

Example 7

Efficacy Study in Terms of Weight Gain of a Composition Comprising Ivermectin and Zeranol in Cattle The object of this comparative study was to evaluate the effect of a composition comprising ivermectin and zeranol according to the invention on weight gain in cattle over a period of ninety days.

The animals had not been treated for parasitic infection or infestation for six month prior to the trial. Three groups of thirty animals (Holstein, generally weighing 250 to 300 kg) received:

Group 1: Ivomec® injectable for Cattle+Ralgro®
Group 2: Composition according to Example 3
Group 3: control (no treatment) Doses:
Ivomec®: 1 ml / 50 kg (subcutaneous route)
Ralgro®: one implant (36 mg zeranol)
Composition according Example 3: 1 ml/50 kg (subcutaneous route), Results (means):

|  | Group 1 | Group 2 Example | Group 3 |
|---|---|---|---|
| Day 1 | 235.46 kg | 243.07 kg | 243.59 kg |
| Day 90 | 285.05 kg | 296.46 kg | 271.73 kg |

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. An injectable composition, comprising:
   a liquid solvent,
   at least one anthelmintic agent selected from the group consisting of avermectins, milbemycins, and derivatives thereof, and
   at least one hormonal growth promoter,
   wherein the anthelmintic agent and the hormonal growth promoter are dissolved in the solvent, and
   wherein the liquid solvent is free of solid or film-forming polymers.

2. The injectable composition of claim 1, wherein the liquid solvent is composed of at least one hydrophilic solvent.

3. The injectable composition of claim 2, wherein the hydrophilic solvent comprises at least one compound selected from the group consisting of a propylene glycol, a polyethylene glycol, di(ethylene glycol)ethyl ether, isopropylidene glycerol, dimethyl isosorbide, propylene carbonate, glycerol, glycofural, pyrrolidones, isopropylidene glycerol, di(propyleneglycol) methyl ether, a C2 to C6 alkanol, acetone, alkyl ester, alkyl ketone, dialylamides, dimethyl sulfoxide, dimethyl sulfone, tetrahydrofuran, cyclic alkyl amide, decylmethylsulfoxide, oleic acid, an aromatic amide, a glycol ethers, di(ethylene glycol)ethyl ether acetate, di(propylene glycol)meyl ether acetate, glycerol formal, glycofurol, isopropyl myristate, and N,N,-dimethylacetamide.

4. The injectable composition of claim 1, wherein the liquid solvent comprises at least one hydrophilic solvent and at least one non-water miscible or hydrophobic solvent.

5. The injectable composition of claim 4, wherein the liquid solvent comprises at least 60% of the hydrophilic solvent.

6. The injectable composition of claim 2, wherein the liquid solvent comprises only one or more hydrophilic solvents.

7. The injectable composition of claim 4, wherein the at least one non-water miscible or hydrophobic solvent comprises one or more compounds selected from the group consisting of triethyl entrate, Miglyol 812, Miglyol 840, Crodamol GTCC, triacetin, benzyl benzoate, a fatty acid, triglyceride, a triester of glycerol, an oil, a sterol, and a higher alkanol.

8. The injectable composition of claim 1, further comprising at least one additional bioactive agent.

9. The injectable composition of claim 1, wherein the anthelmintic agent comprises one or more compounds selected from the group consisting of ivermectin, abamectin, doramectin, eprinomectin, selamectin, milbemycin oxime, and moxidectin.

10. The injectable composition of claim 1, wherein the anthelmintic agent is doramectin.

11. The injectable composition of claims 1, wherein the anthelmintic agent is ivermectin.

12. The injectable composition of claim 1, wherein the anthelmintic agent is moxidectin.

13. The injectable composition of claim 1, wherein the hormonal growth promoter comprises one or more compounds selected from the group consisting of estradiol, estradiol benzate, 17beta-estradiol, trenbolone acetate, zeranol, MGA, progesterone, testosterone and a derivative thereof.

14. The injectable composition of claim 1, wherein the hormonal growth promoter is a combination of estradiol benzoate and progesterone.

15. The injectable composition of claim 1, wherein the hormonal growth promoter is trenbolone acetate.

16. The injectable composition of claim 1, wherein the hormonal growth promoter is zeranol.

17. The injectable composition of claim 1, which comprises 0.2 to 20 wt % of the anthelmintic agent.

18. The injectable composition of claim 1, which comprises 0.2 to 20 wt % of the hormonal growth promoter.

19. The injectable composition of claim 1, which comprises
    0.2 to 20 wt % of the at least one anthelmintic agent, and
    0.2 to 20 wt % of the at least one hormonal growth promoter.

20. The injectable composition of claim 1, wherein the anthelmintic agent is ivermectin and the hormonal growth promoter is zeranol.

21. The injectable composition of claim 20, wherein the liquid solvent comprises benzyl alcohol and glycerol formal.

22. The injectable composition of claim 1, wherein the liquid solvent comprises benzyl alcohol and glycerol formal.

23. A method of promoting animal growth comprising administering an effective amount of the composition of claim 1 to an animal.

24. The method of claim 23, wherein the animal is a food animal.

25. The method of claim 23, wherein the food animal is selected from the group consisting of cattle, sheep, pigs, chickens, turkeys, and rabbits.

26. A method of simultaneously promoting growth of an animal and treating or preventing parasitic infections and/or infestations in an animal, comprising administering an effective amount of the composition of claim 1 to said animal.

27. The method of claim 26, wherein the animal is a food animal.

28. The method of claim 27, wherein the food animal is selected from the group consisting of cattle, sheep, pigs, chickens, turkeys, and rabbits.

29. The method of claim 23, wherein said composition is administered intramuscularly.

30. The method of claim 23, wherein said composition is administered intraperitoneally.

31. The method of claim 23, wherein said composition is administered subcutaneously.

32. The method of claim 23, wherein said composition is administered to one or more horses.

33. The method of claim 23 wherein said composition is administered to one or more cattle.

34. The method of claim 23, wherein said composition is administered to one or more bison.

35. The method of claim 23, wherein said composition is administered to one or more reindeer.

36. The method of claim 23, wherein said composition is administered to one or more deer.

37. The method of claim 23, wherein said composition is administered to one or more goats.

38. The method of claim 23, wherein said composition is administered to one or more sheep.

39. The method of claim 23, wherein said composition is administered to one or more camels.

40. The method of claim 23, wherein said composition is administered to one or more swine.

41. The method of claim 23, wherein said composition is administered to one or more rabbits.

42. The method of claim 23, wherein said composition is administered to one or more chickens.

43. The method of claim 23, wherein said composition is administered to one or more turkeys.

44. The composition of claim 8, wherein the bioactive agent is one or more antibiotic(s).

45. The composition of claim 8, wherein the bioactive agent is one or more vaccine(s).

46. The composition of claim 8, wherein the bioactive agent is one or more antiparastic agent(s).

* * * * *